(12) United States Patent
Choe et al.

(10) Patent No.: US 9,144,396 B2
(45) Date of Patent: Sep. 29, 2015

(54) APPARATUS AND METHOD OF ANALYZING CONSTITUENTS OF GAS IN ORAL CAVITY AND ALVEOLAR GAS

(75) Inventors: Yong Sahm Choe, Gyeonggi-do (KR); Chang Sik Lee, Gyeonggi-do (KR); Je Young Youn, Seoul (KR); Young Sun Kang, Gyeonggi-do (KR)

(73) Assignee: Yong Sahm Choe, Gyeonggi-Do (KR)

( * ) Notice: Subject to any disclaimer, the term of this patent is extended or adjusted under 35 U.S.C. 154(b) by 755 days.

(21) Appl. No.: 12/673,851

(22) PCT Filed: Aug. 20, 2008

(86) PCT No.: PCT/KR2008/004833
§ 371 (c)(1),
(2), (4) Date: Feb. 17, 2010

(87) PCT Pub. No.: WO2009/025488
PCT Pub. Date: Feb. 26, 2009

(65) Prior Publication Data
US 2011/0021942 A1   Jan. 27, 2011

(30) Foreign Application Priority Data

Aug. 20, 2007 (KR) .................. 10-2007-0083383
Aug. 19, 2008 (KR) .................. 10-2008-0080918

(51) Int. Cl.
*A61B 5/08*   (2006.01)
*A61B 5/097*   (2006.01)
*G01N 33/497*   (2006.01)
*G01N 1/22*   (2006.01)
*G01N 30/20*   (2006.01)

(52) U.S. Cl.
CPC .............. *A61B 5/097* (2013.01); *G01N 33/497* (2013.01); *G01N 1/2226* (2013.01); *G01N 2001/2244* (2013.01); *G01N 2030/207* (2013.01)

(58) Field of Classification Search
CPC ........... A61B 5/097; G01N 2001/2244; G01N 1/2226; G01N 2030/207
USPC .............. 600/529–543; 73/23.3, 23.35–23.42
See application file for complete search history.

(56) References Cited

U.S. PATENT DOCUMENTS 3,883,739 A * 5/1975 Jenkins .......................... 250/304
4,017,373 A    4/1977 Shaw et al.
5,425,374 A * 6/1995 Ueda et al. ..................... 600/532

(Continued)

FOREIGN PATENT DOCUMENTS

KR   10-2004-0091837   11/2004

OTHER PUBLICATIONS

"Gas Chromatography." Wikipedia.org.*

*Primary Examiner* — Patricia Mallari
*Assistant Examiner* — Tiffany Weston
(74) *Attorney, Agent, or Firm* — Revolution IP, PLLC

(57) ABSTRACT

An apparatus and a method of analyzing constituents of gas in an oral cavity and exhaled breath is disclosed. The apparatus for analyzing the constituents of gas in the oral cavity and exhaled breath according to the present invention includes a filter to filter the outside gas by adsorbing polar molecules and non-polar molecules in the outside air and by removing water in the outside air in order to use the outside gas as carrier gas. The apparatus can also include a plurality of solenoid valves for controlling the flow of a carrier gas; a sensor for detecting components of the exhaled breath; a pump to draw the gas in the oral cavity or the exhaled breath and the carrier gas and discharge the gases to the outside; a control unit for controlling the components of the apparatus; and a display device to display results calculated by the control unit.

14 Claims, 12 Drawing Sheets

(56) References Cited

U.S. PATENT DOCUMENTS

| | | | |
|---|---|---|---|
| 5,922,610 A * | 7/1999 | Alving et al. | 436/116 |
| 6,148,657 A * | 11/2000 | Satoh et al. | 73/23.35 |
| 6,341,520 B1 * | 1/2002 | Satoh et al. | 73/23.35 |
| 6,899,684 B2 | 5/2005 | Mault et al. | |
| 2004/0133116 A1 * | 7/2004 | Abraham-Fuchs et al. | 600/532 |
| 2007/0062255 A1 | 3/2007 | Talton | |

* cited by examiner

[Fig. 3]
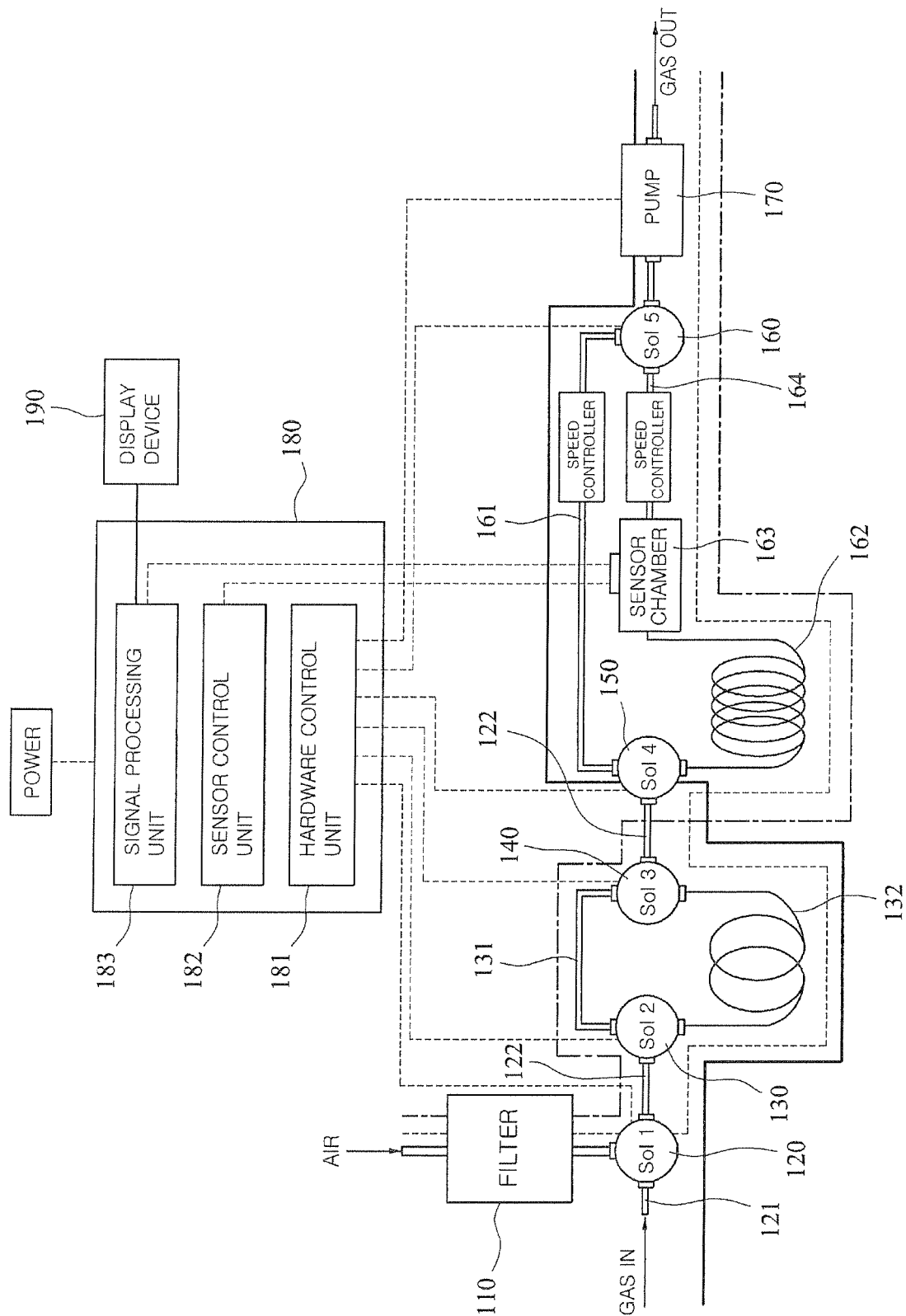

[Fig. 4]
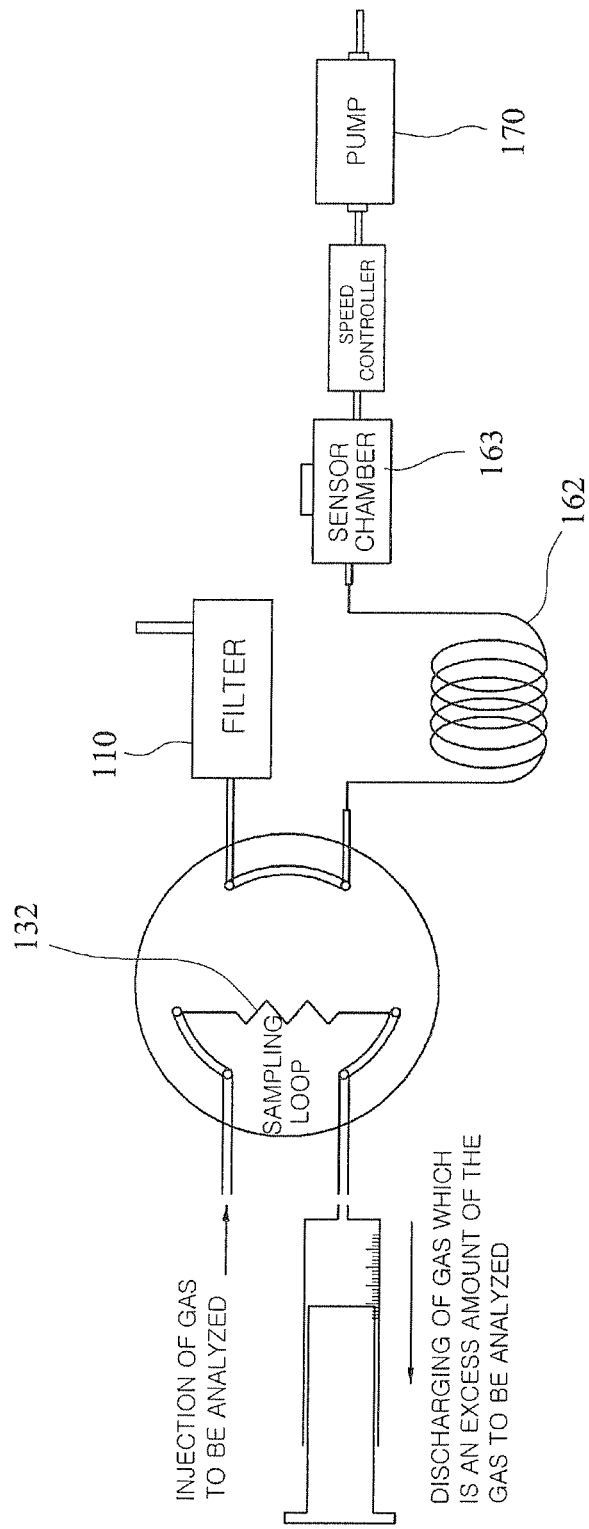

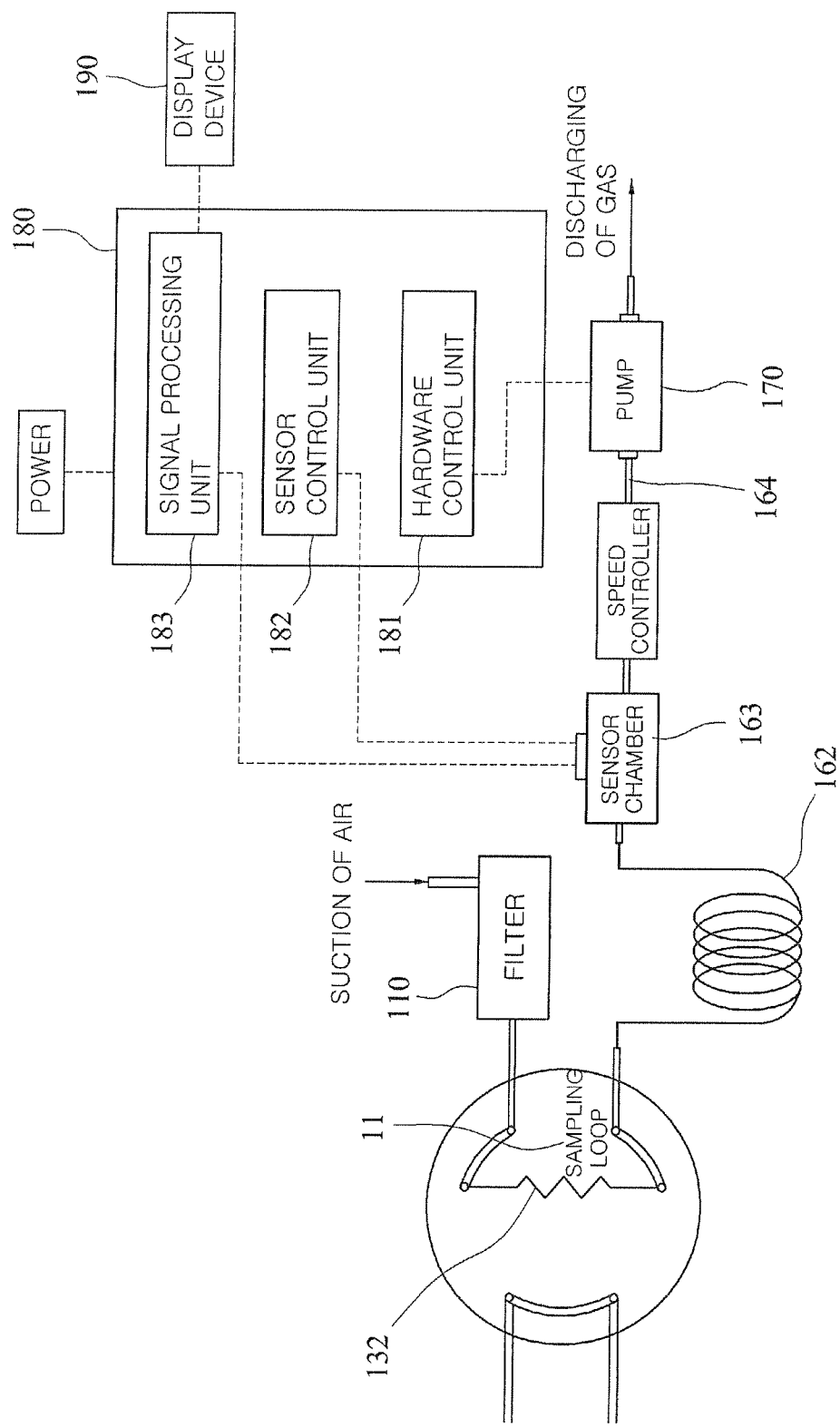
[Fig. 5]

[Fig. 6]
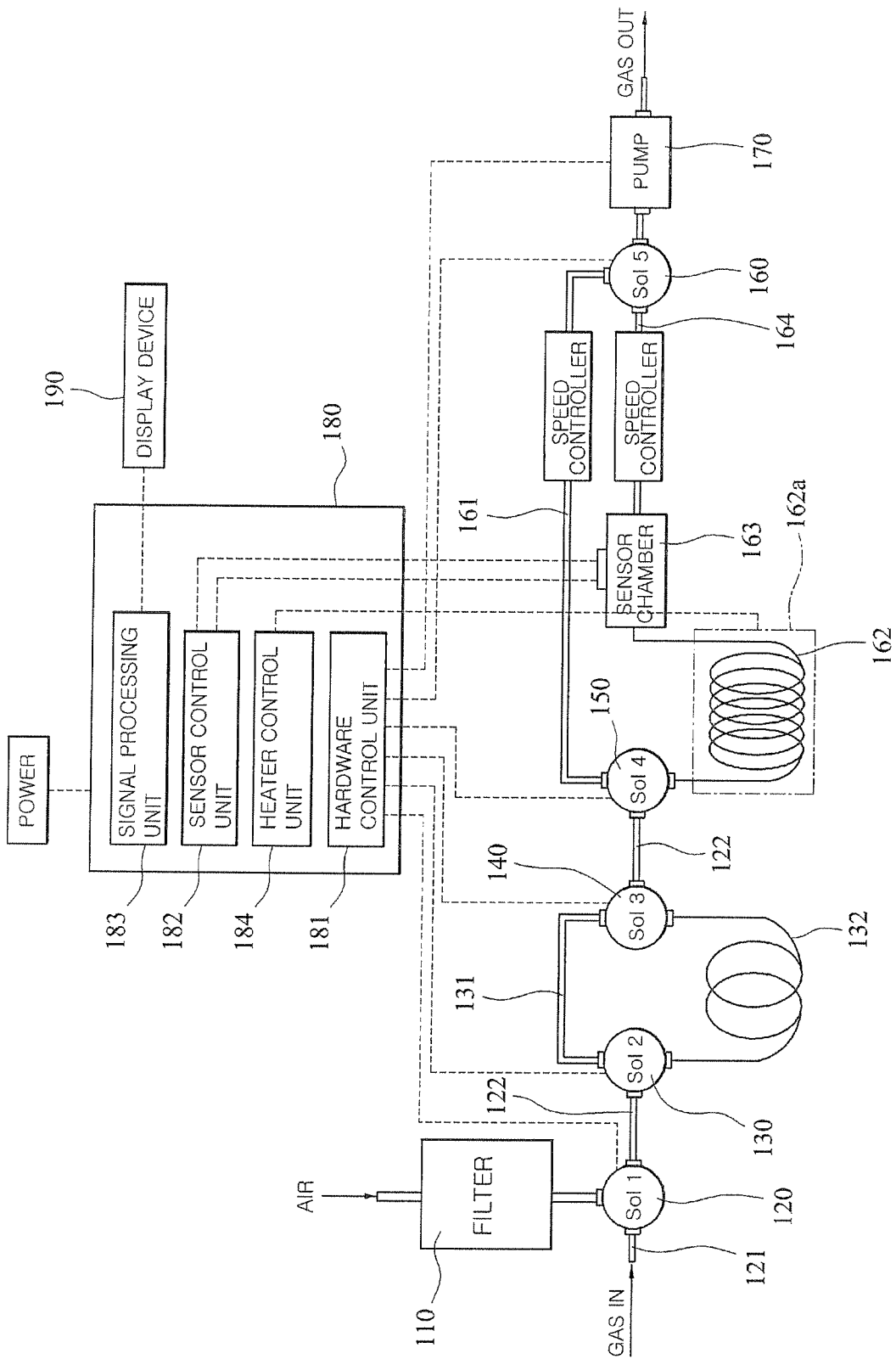

[Fig. 7]
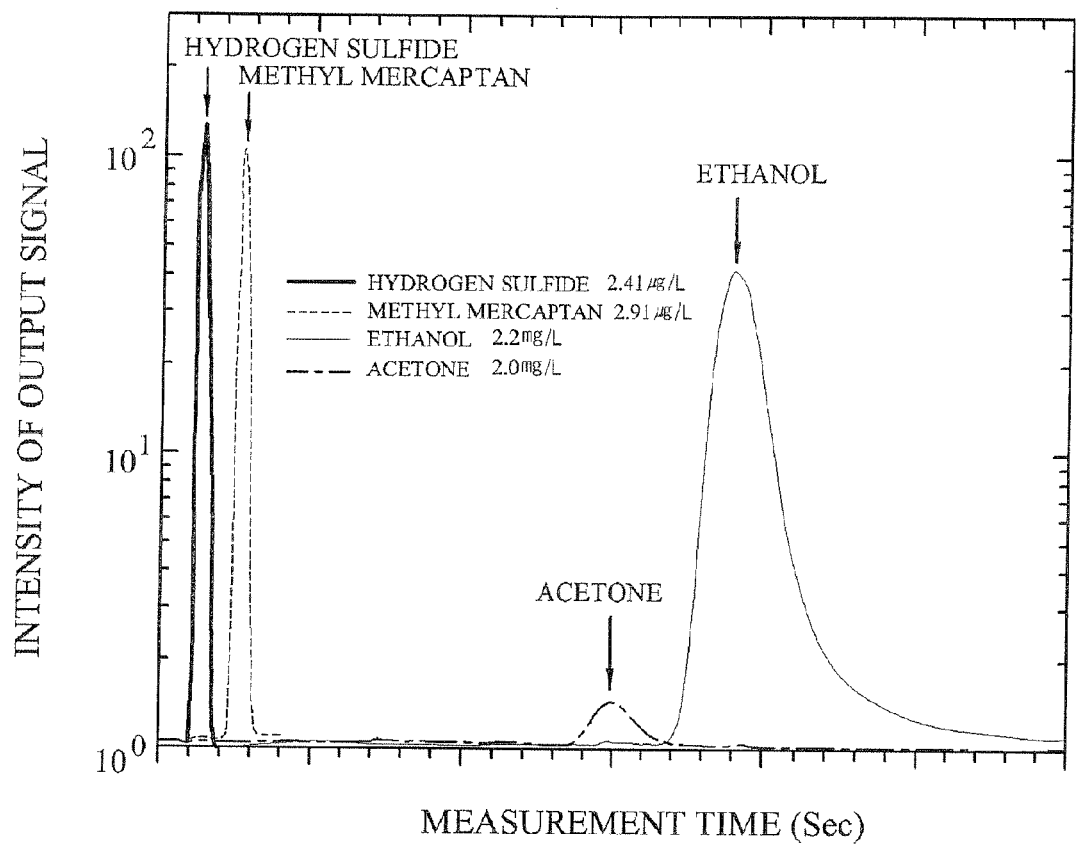

[Fig. 8]
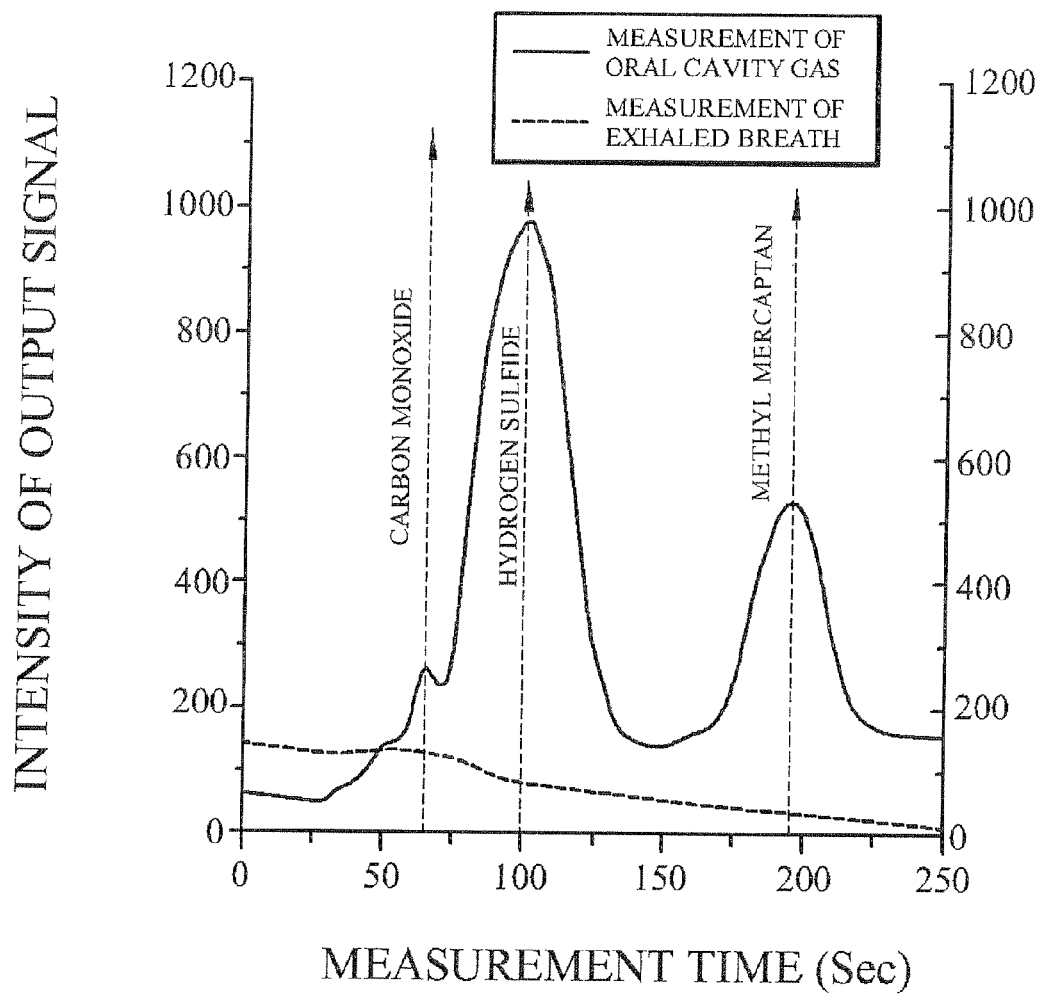

[Fig. 9]
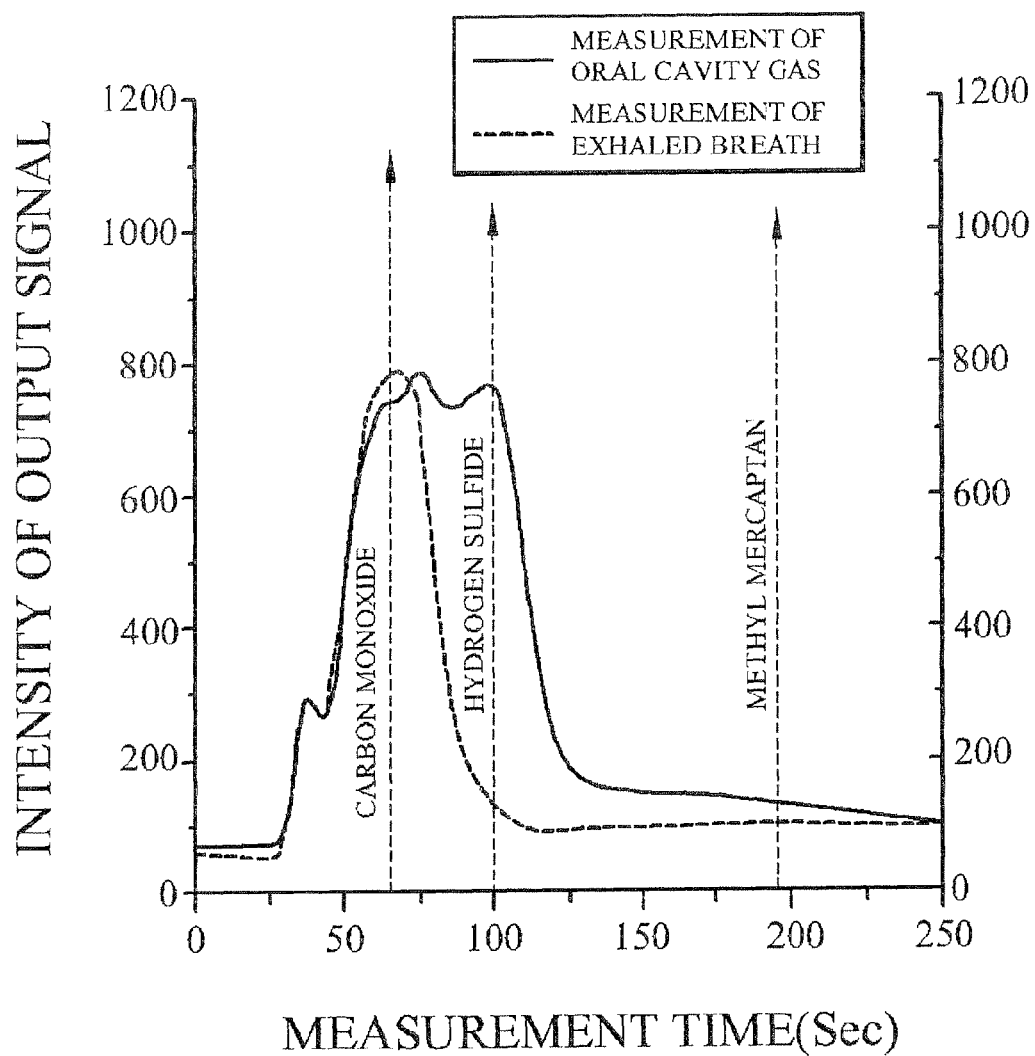

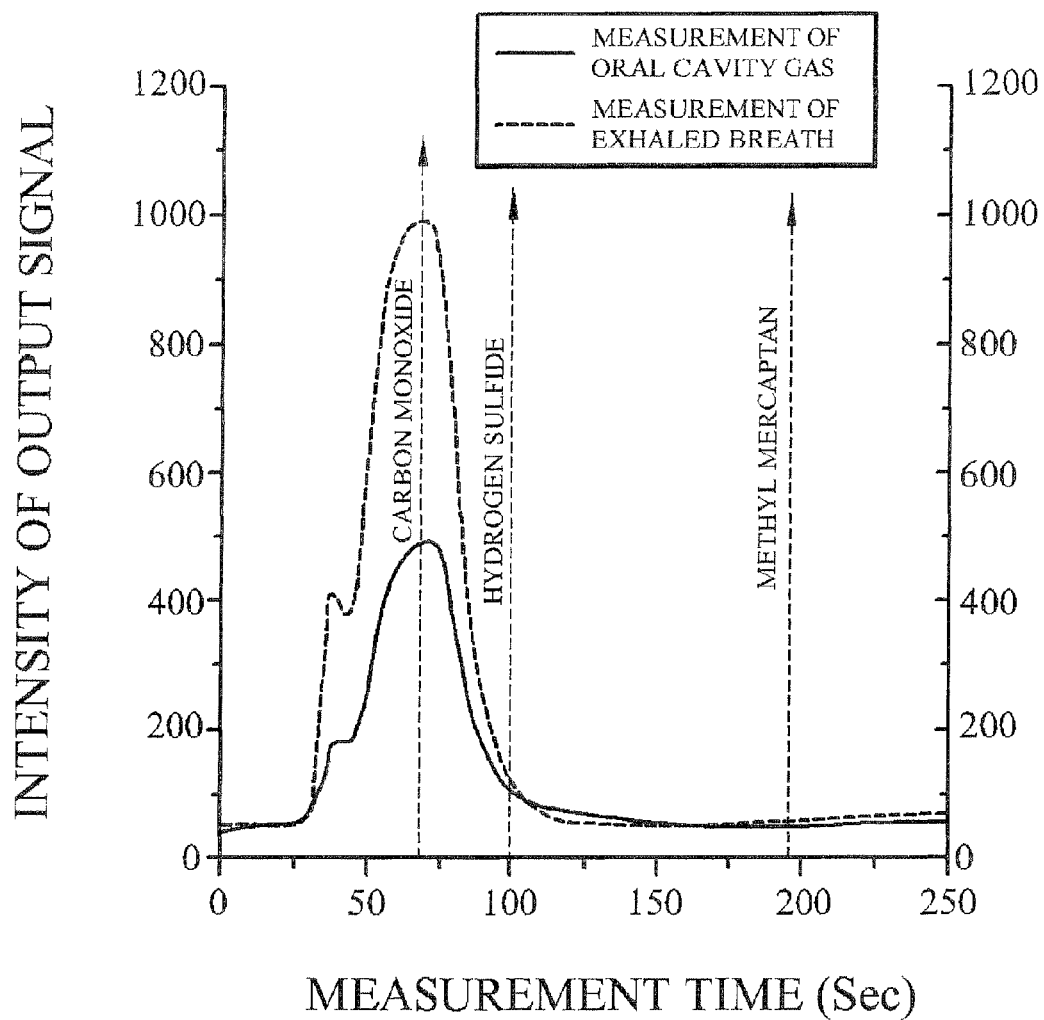
[Fig. 10]

[Fig. 11]
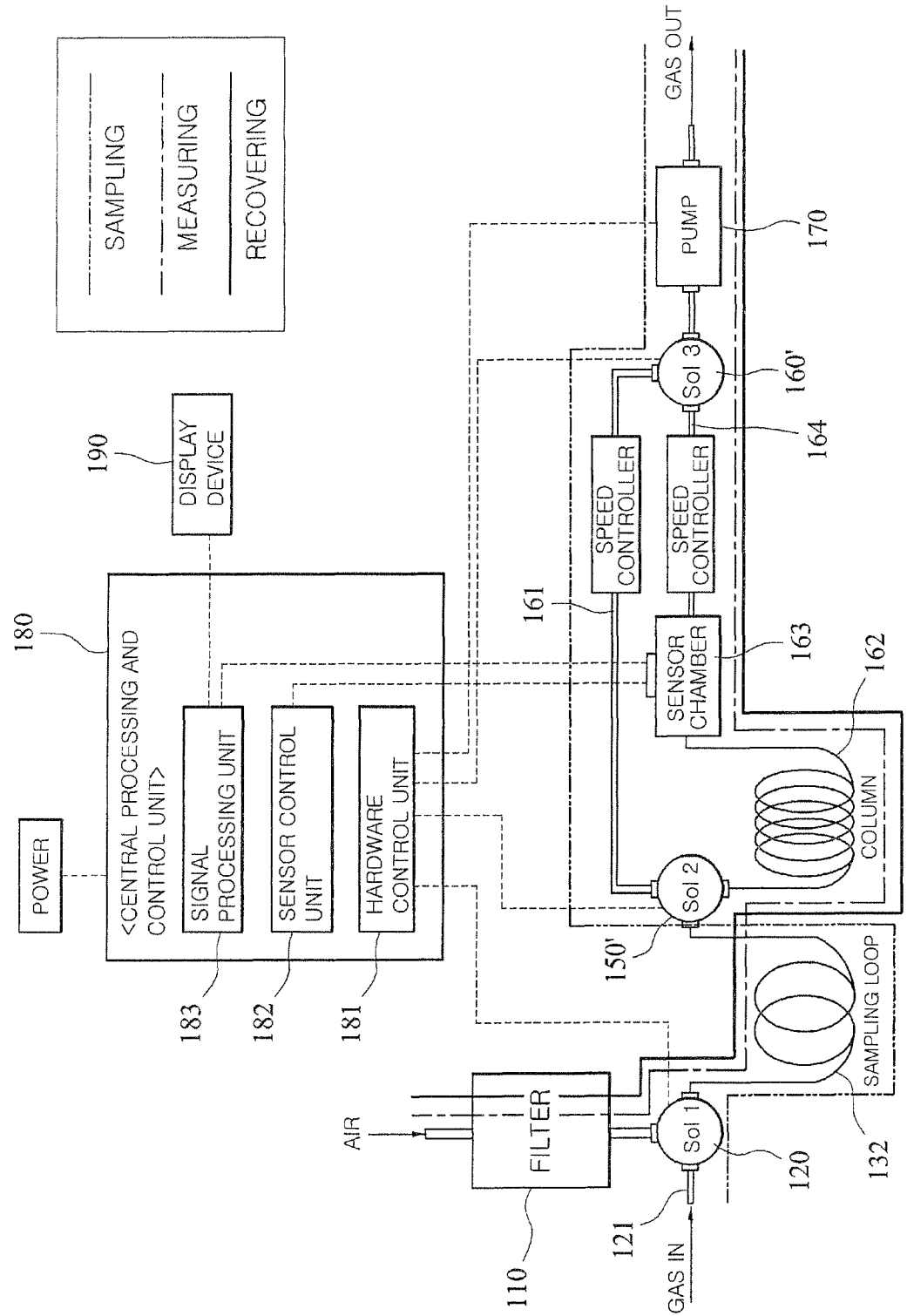

[Fig. 12]
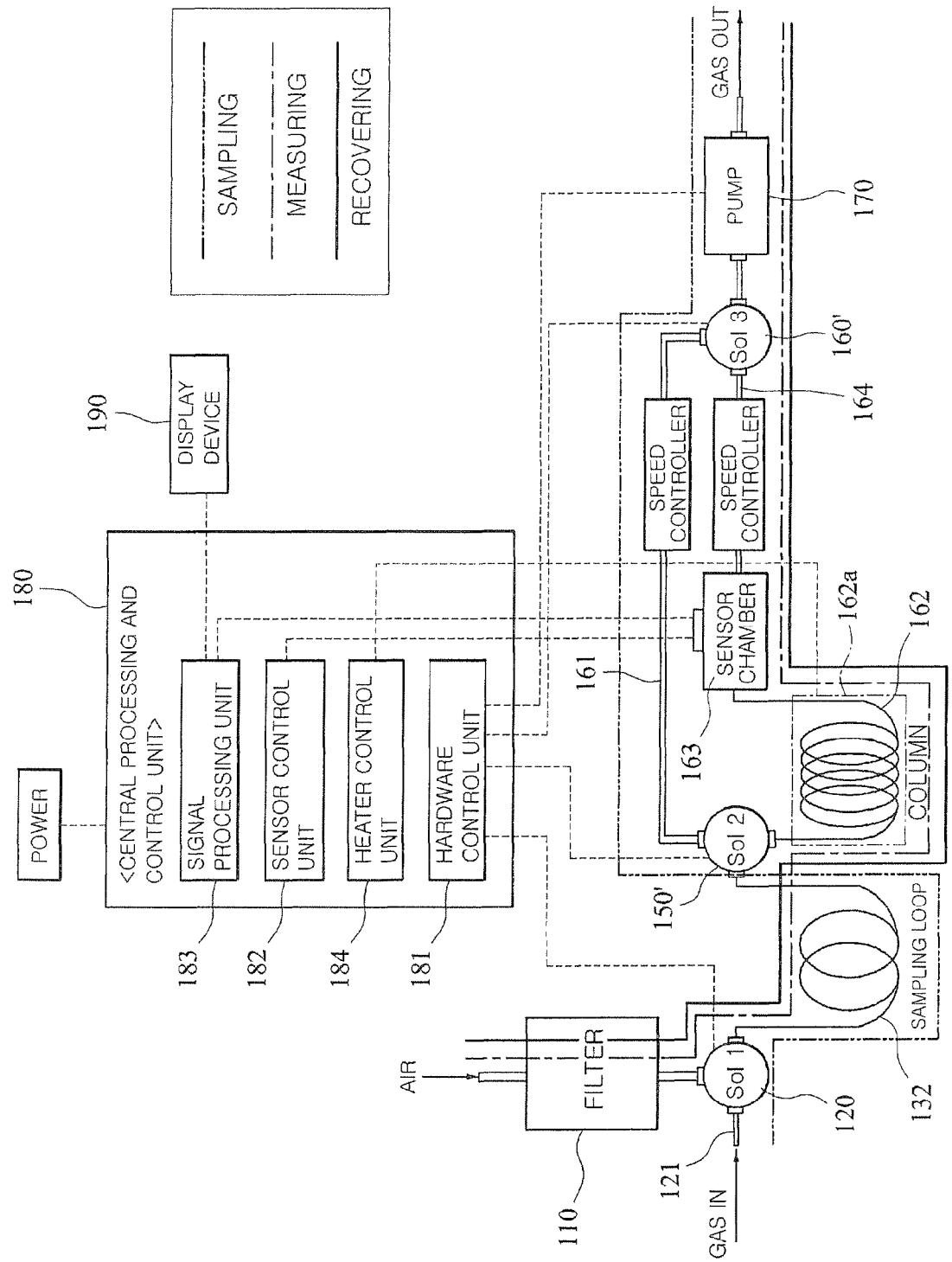

[Fig. 13]
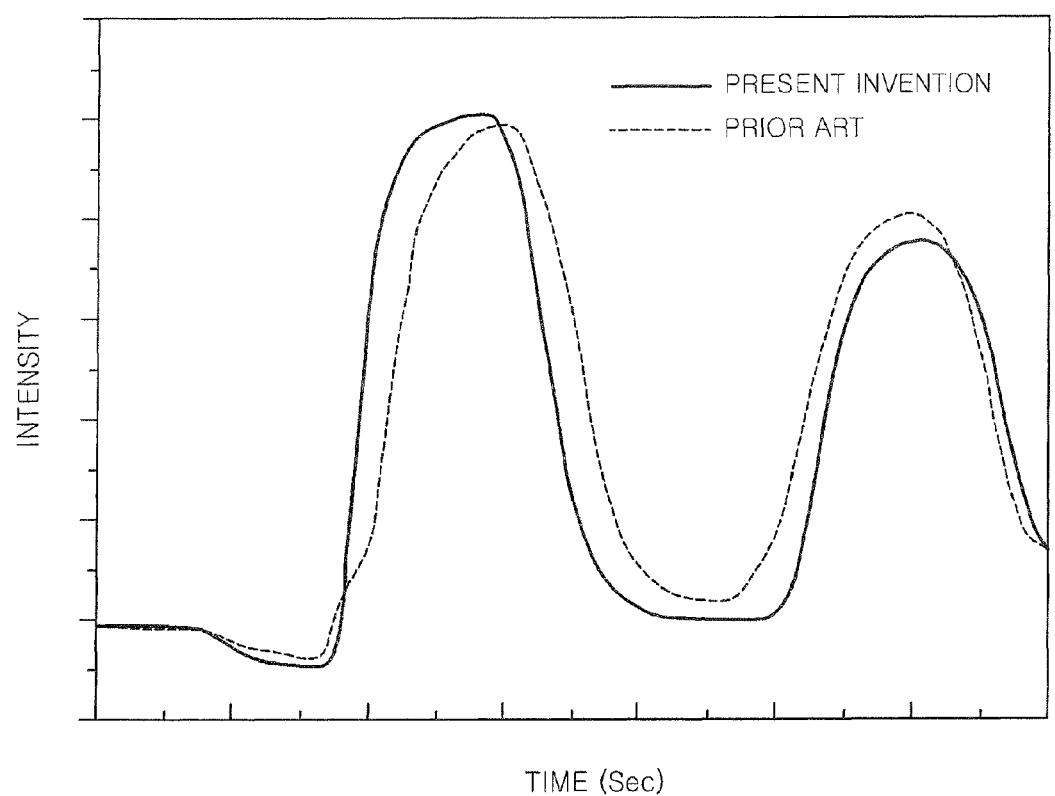

APPARATUS AND METHOD OF ANALYZING CONSTITUENTS OF GAS IN ORAL CAVITY AND ALVEOLAR GAS

CROSS-REFERENCE TO RELATED APPLICATIONS

This application is a §371 national stage entry of International Application No. PCT/KR2008/004833, filed Aug. 20, 2008, which claims priority to Korean Patent Application No. 10-2007-0083383, filed Aug. 20, 2007, and Korean Patent Application No. 10-2008-0080918, filed Aug. 19, 2008, all of which are hereby incorporated by reference.

TECHNICAL FIELD

The present invention relates to an apparatus and a method of analyzing constituents of gas in an oral cavity and exhaled breath. The apparatus is used to analyze constituents of volatile sulfur compounds such as hydrogen sulfide and methyl mercaptan, volatile organic compounds such as ethanol and acetone, and other gases such as carbon monoxide contained in the gas in the oral cavity and exhaled breath and to separately measure concentrations of the gases.

BACKGROUND ART

In general, gas in an oral cavity means gas which is generated from an oral cavity of humans. Oral malodor, a kind of halitosis consists mostly of volatile sulfur compounds like hydrogen sulfide and methyl mercaptan generated from the oral cavity due to the anaerobic breakdown of proteins into individual amino acids which is caused by tongue coating or periodontal diseases.

Meanwhile, exhaled breath which is generated while humans breathe is discharged through an oral cavity and a nasal cavity to the outside, and contains gas constituents relating to human metabolism and respiration. In particular, a patient having an internal disease expels a bad smell containing volatile organic compounds such as acetone and alcohol, ammonia and the like according to the type of disease and inflammation. It is well known in the related art that constituents of gas, which is generated from an oral cavity or discharged through an oral cavity or a nasal cavity while breathing, relate to the nature of diseases. For example, a physiological phenomenon of when a tongue is coated at a lower side thereof generates hydrogen sulfide, a pathological phenomenon of when periodontal disease occurs generates methyl mercaptan, aceton relates to diabetes, and ammonia relates to a kidney disease. Furthermore, measurement of the concentration of carbon monoxide of exhaled breath of humans is considered a method of objectively evaluating a smoking condition. Accordingly, if predetermined constituents of gas in an oral cavity or exhaled breath are analyzed and their concentrations are measured, it is possible to schematically diagnose an oral cavity disease and an internal disease of humans. The diagnosis method may be useful in diagnosing an internal disease of a patient having oral malodor and a disease of infants or patients in the intensive care unit who are difficult to communicate to doctors. The method can also be used to diagnose the condition of a disease of domestic animals.

It is necessary to use a very precise and high-sensitive measuring apparatus in order to analyze the gas in the oral cavity or the exhaled breath of humans. Currently, in order to separate the gas constituents from each other, a gas chromatography is used. In order to quantitatively analyze the separated gas constituents, it is necessary to use various types of detectors such as a thermal conductive detector, a flame ionization detector, an electron capture detector, a flame photoelectronic detector, and a heat ionization detector, or a mass spectrometry detector.

The above-mentioned analysis apparatuses are costly and operated by professionals having specific knowledge and technique regarding the apparatuses, which causes an increase in the cost of operation. For this reason, the apparatuses are used only by a small minority of research organizations.

In order to avoid the above-mentioned problems of the gas chromatography, a portable and standalone type of oral malodor measuring apparatus is provided to clinicians or hospitals to measure gas in the oral cavity. For example, gas analyzing apparatuses such as Halimeter (Interscan Corporation in the USA) are extensively used.

In respects to a known oral malodor measuring apparatus, an electrochemical gas sensor that senses oral malodor is disclosed in U.S. Pat. No. 4,017,373. In this invention, only the total amount of volatile sulfur compounds of the sensed oral malodor gas is displayed. For this reason, there is a problem in that hydrogen sulfide ($H_2S$) and methyl mercaptan ($CH_3SH$) cannot be discriminated from each other. That is, whether the oral malodor of the patient is based on a physiological factor or a pathological factor cannot be determined; as a result, the patient cannot be precisely diagnosed. Furthermore, the amount of oral malodor gas which is to be measured is 500 ml or more. For this reason, the concentration of oral malodor may be reduced due to the air around the measuring apparatus. As a result, the constituents of oral malodor cannot be precisely analyzed and malfunction of the apparatus may occur due to gas constituents in the air.

In addition, FIG. 1 illustrates another apparatus for monitoring oral malodor gas. In the apparatus, if patient bite a mouthpiece 1 to analyze oral malodor, an oral malodor gas is transferred through a mouth filter 2 in the mouthpiece 1 by pump 4, and then constituents of oral malodor gas is analyzed by using a sensor 5. An electromagnetic valve 3 is opened, and a pump 4 is operated to refresh the sensor 5 by using the air that is filtered by a carbon filter. In the apparatus, a portion of effective volatile sulfur compounds of the oral malodor gas is adsorbed on the mouth filter 2 in the mouthpiece 1 during sampling of the oral malodor gas. Therefore, it is difficult to precisely analyze the oral malodor gas. Furthermore, the sampling amount of oral malodor gas is used 80 ml. For this reason, it is difficult to precisely analyze the volatile sulfur compounds. In addition, the only total amount of volatile sulfur compounds such as hydrogen sulfide or methyl mercaptan is displayed in the apparatus. For this reason, patients having physiological oral malodor and pathological oral malodor cannot be distinguished from each other.

In order to avoid the above-mentioned problems, that is, a difficulty in discriminating between the physiological and pathological oral malodors of the gas in the oral cavity, Korean Patent Application No. 2004-91837 discloses an apparatus for analyzing constituents of oral malodor gas. The apparatus shown in FIG. 2 is provided with a first three way valve 12 that is connected to a control valve 12a at an end thereof, to a mouthpiece tube at another end thereof, and to an end of a sampling loop 11 for storing sampled oral malodor gas at a third end thereof, a second three way valve 16 that is connected to another end of the sampling loop 11 connected to the third end of the first three way valve 12 at an end thereof, to a syringe 14 through a check valve 13 at another end thereof to absorb the oral malodor gas and then store the absorbed oral malodor gas in the sampling loop 11, and to a solenoid valve 15 at a third end thereof, a third three way valve 20 that is connected to a solenoid valve 15 at an end thereof, to an air flow tube 17 through which the filtered air flows at another end thereof, to a tube 19 connected to a semiconductor sensor 18 at a third end thereof, an air filter 22 that is connected to an end of the air flow tube 17 to filter the air, a suction pump 21 that is connected to another end of the semiconductor sensor 18 to pass the air and the diluted oral malodor gas through the semiconductor sensor 18, and a speed controller 23 that is connected to an end of the air filter 22 to control an amount of air so that a ratio of the oral malodor gas provided from the solenoid valve 15 and the air is in the range of 1:1 to 1:2.

If the mixing ratio of the oral malodor gas and the filtered air is very low, the relative humidity is insignificantly reduced. However, if the mixing ratio of the oral malodor gas and the filtered air is very high, the oral malodor gas is excessively diluted to have a significantly reduced concentration. For this reason, it is preferable to control the ratio by using the speed controller 23 so that the ratio is in the range of 1:1 to 1:2.

Additionally, in a known invention, the air filter 22 is used to recover a gas sensor after gas analysis. However, in the invention of the above-mentioned patent, the air filter 22 is used to reduce the relative humidity of sampled oral malodor gas. In particular, in the known invention, the oral malodor gas is analyzed while a patient opens his mouth. Therefore, various types of gases in the air may be mixed with the oral malodor gas. However, in the invention of the above-mentioned patent, a filter that is formed of silica gel and activated carbon is used to filter unknown gas constituents in the air and to mix the filtered air and the oral malodor gas, which enables the oral malodor gas to be precisely analyzed.

If the oral malodor gas is analyzed, the relative humidity in the oral cavity is almost 100% at a body temperature of 36.5° C. Accordingly, if the oral malodor gas is inhaled into an apparatus for analyzing oral malodor at room temperature in the range of 20 to 28° C., water condenses at the surface of the sensor, which erroneously outputs sensor signal. In order to avoid this, in the present invention, the air filter 22 including silica gel is used to filter the air before the air is inhaled into the apparatus, and the filtered air is mixed with the oral malodor gas to reduce the relative humidity at the sensor, thus preventing water from condensing on the surface of the sensor.

The semiconductor sensor 18 is provided with a oral malodor gas measurement unit 18a that includes a gas sensor having predetermined selectivity in respects to hydrogen sulfide, and an oral malodor gas measurement unit 18b that includes a sensor having predetermined selectivity in respects to methyl mercaptan.

However, in the above-mentioned known configuration, the apparatus for analyzing the constituents of the oral malodor gas can only analyze only physiological oral malodor gas and pathological oral malodor gas of a patient, which are two types of oral malodor gases in the oral cavity, but cannot analyze other volatile organic compounds of the gas in the oral cavity and constituents of the exhaled breath.

In addition, it is required that the two types of sensors used to analyze two types of gases have selective reactivity in respects to the gases. Accordingly, the selection of the sensor is limited. The wrong selection of the sensor increases the possibility for error in terms of measured value, thus disturbing a precise analysis.

In order to overcome the above problems, there has been applied KR Patent Application No. 10-2007-83383 by the present applicant as shown in FIG. 3, which is related to a gas analyzing apparatus of the oral cavity gas and the exhaled breath comprising a filter 110 that is filled with an adsorption and dehumidifying substance such as silica gel, calcium chloride, and activated carbon to filter the outside gas by adsorbing polar molecules and non-polar molecules in the outside air and by removing water in the outside air in order to use the outside gas as carrier gas, a first solenoid valve 120 that is connected to the filter 110 at an end thereof so as to provide carrier gas passing through the filter 110 thereinto and controls a flow of the gas in the oral cavity or the exhaled breath flowing through a connection port 121 thereto; a second solenoid valve 130 that is connected through a connection tube 122 to the first solenoid valve 120 at a first port thereof, connected through a bypass tube 131 to a third solenoid valve 140 at a second port thereof so as to bypass the carrier gas, and connected to a sampling loop filled with the gas in the oral cavity or the exhaled breath collected by the third solenoid valve 140 at a third port thereof; a fourth solenoid valve 150 that is connected through the connection tube 122 to the third solenoid valve 140; a fifth solenoid valve 160 that is connected through an upper bypass tube 161 provided with a speed controller to a port of the fourth solenoid valve 150; a column 162 that is connected to another port of the fourth solenoid valve 150 to allow the gas in the oral cavity or the exhaled breath and the carrier gas to sequentially flow therethrough; a sensor chamber 163 that is connected to the column at an end thereof and has a sensor; a lower bypass tube 164 that is connected to another end of the sensor chamber at an end thereof and to the fifth solenoid valve 160 at another end thereof and is provided with another speed controller; a pump 170 that is connected to the fifth solenoid valve 160 to draw the gas in the oral cavity or the exhaled breath and the carrier gas and then discharge the gas in the oral cavity or the exhaled breath and the carrier gas to the outside; a control unit 180 that is connected to the first to the fifth solenoid valves 160, the sensor chamber 163, and the pump 170 to control the first to the fifth solenoid valves 120, 130, 140, 150 and 160, the sensor chamber 163, and the pump 170; and a display device 190 that measures concentrations of the gases by using signal and calculation treatments in the control unit 180 to display results.

In the above structure, the bypass tube 131 that bypasses the carrier gas functions as follows. First, the bypass tube 131 prevents the inside of the sampling loop 132 from being contaminated by residues and impurities probably contained in the carrier gas. Second, when residues by the collected gas remain in the sampling loop 132, the bypass tube 131 prevents the residues from polluting the column 162.

However, the bypass tube 131 can be omitted as long as there is no risk of contamination of the sampling loop 132 by the carrier gas and the collected gas. According to this, the second solenoid valve 130 and the third solenoid valve 140 can be removed.

The above structure is disclosed in KR Patent Application No. 10-2008-0080918 filed on the basis of the priority of KR Patent Application No. 10-2007-83383 and illustrated in FIG. 11 through FIG. 13 of the present invention.

DISCLOSURE OF INVENTION

Technical Problem

The present invention has been made keeping in mind the above problems occurring in the related arts, and an object of the present invention is to provide an apparatus and a method of analyzing constituents of gas in an oral cavity and exhaled breath, so that volatile sulfur compounds such as hydrogen sulfide and methyl mercaptan, volatile organic compounds, and other gas constituents such as carbon monoxide are separately measured to analyze gas in an oral cavity and exhaled breath, thereby diagnosing oral health and internal diseases.

The analyzing apparatus according to an embodiment of the invention requires a bypass tube and five solenoid valves. On the other hand, according to another embodiment of the present invention, the desired effect can be obtained with only three solenoid valves, also omitting the bypass tube.

Technical Solution

In order to accomplish the above object for the first embodiment, an apparatus for analyzing constituents of gas in an oral cavity and exhaled breath according to the present invention includes a filter that is filled with a substance adsorbing a polar molecule and a non-polar molecule including silica gel and activated carbon to filter an outside carrier gas; a first solenoid valve that is connected to the filter at an end thereof so as to provide carrier gas passing through the filter thereinto and controls a flow of the gas in the oral cavity or the exhaled breath flowing through a connection port thereto; a second solenoid valve that is connected through a connection tube to the first solenoid valve at a first port thereof, connected through a bypass tube to a third solenoid valve at a second port thereof so as to bypass the carrier gas, and connected to a sampling loop 132 filled with the gas in the oral cavity or the exhaled breath collected by the third solenoid valve at a third port thereof; a fourth solenoid valve that is connected through the connection tube to the third solenoid valve; a fifth solenoid valve that is connected through an upper bypass tube provided with a speed controller to a port of the fourth solenoid valve; a column that is connected to another port of the fourth solenoid valve to allow the gas in the oral cavity or the exhaled breath and the carrier gas to sequentially flow therethrough; a sensor chamber that is connected to the column at an end thereof and has a sensor; a lower bypass tube that is connected to another end of the sensor chamber at an end thereof and to the fifth solenoid valve at another end thereof and is provided with another speed controller; a pump that is connected to the fifth solenoid valve to draw the gas in the oral cavity or the exhaled breath and the carrier gas and then discharge the gas in the oral cavity or the exhaled breath and the carrier gas to the outside; a control unit that is connected to the first to the fifth solenoid valves, the sensor chamber, and the pump to control the first to the fifth solenoid valves, the sensor chamber, and the pump; and a display device that measures concentrations of the gases by using signal and calculation treatments in the control unit to display results.

In order to accomplish the above object for the second embodiment, an apparatus for analyzing constituents of a gas in an oral cavity and an exhaled breath, the apparatus comprising a filter that is filled with a substance such as silica gel and activated carbon to filter off a carrier gas at the outside; a first solenoid valve that is connected to the filter at an end thereof so as to provide the carrier gas passed through the filter thereinto and controls a flow of the gas in the oral cavity or the exhaled breath flowing through a connection port thereto; a sampling loop that is connected with the first solenoid valve and filled with the collected gas in the oral cavity or carrier gas; a second solenoid valve that is connected to opposite side of the sampling loop; a third solenoid valve that is connected to another port of the second solenoid valve through the medium of an upper bypass tube provided with a speed controller; a column that is connected to another port of the second solenoid valve to allow the gas in the oral cavity or the exhaled breath and the carrier gas to sequentially flow therethrough; a sensor chamber that has a sensor connected to the column at an end thereof; a lower bypass tube that is connected to another end of the sensor chamber at an end thereof and to the third solenoid valve at another end thereof and is provided with another speed controller; a pump that is connected to the third solenoid valve to draw the gas in the oral cavity or the exhaled breath and the carrier gas and then discharge the gas in the oral cavity or the exhaled breath and the carrier gas to the outside; a control unit that is connected to the first to the third solenoid valves, the sensor chamber, and the pump to control the first to the third solenoid valves, the sensor chamber, and the pump; and a display device that measures concentrations of the gases by using signal and operation processed in the control unit to display the results.

A method of analyzing constituents of gas in an oral cavity and exhaled breath according to the present invention includes sampling the gas in the oral cavity or the exhaled breath from oral cavities or nasal cavities of humans or domestic animals; storing the sampled gas in a sampling loop; generating a fresh carrier gas from a filter; inhaling the generated carrier gas by using a pump; and providing the absorbed carrier gas to a column that is filled with a packing material for gas chromatography columns in conjunction with the gas collected in the sampling loop by using the pump to separate gas constituents from each other by using a difference in retention time and to measure concentrations of the separated gas constituents by using a gas sensor.

Advantageous Effects

In an apparatus and a method of analyzing constituents of gas in an oral cavity and exhaled breath according to the present invention, gas can be sampled from oral cavities of mouths of humans or domestic animals and exhaled breath can be sampled from noses thereof, and provided to a column that is designed so that carrier gas moves by using a small motor pump and is filled with a packing material for gas chromatography in conjunction with fresh dry air that is used as carrier gas and passes through a filter instead of high-pressure inert gas. The gas constituents are separated from each other by using a difference in retention time of the gas constituents in the column, and concentrations of the separated gas constituents are measured by using a gas sensor to analyze a volatile organic compound, carbon monoxide, and other gas constituents of oral malodor gas in an oral cavity and exhaled breath, thereby diagnosing oral cavity and internal diseases and performing observation so as to make a diagnosis on diseases.

BRIEF DESCRIPTION OF THE DRAWINGS

FIG. 3 is a view illustrating an apparatus for analyzing constituents of gas in an oral cavity and exhaled breath according to a first embodiment of the present invention;

FIG. 4 is a view illustrating an operation of a solenoid valve when gas in an oral cavity is sampled according to the present invention;

FIG. 5 is a view illustrating an operation of a solenoid valve during a measuring step after gas in the oral cavity and exhaled breath are sampled according to the present invention;

FIG. 6 is a view illustrating an apparatus for analyzing constituents of gas in the oral cavity and exhaled breath according to a modified embodiment of the first embodiment of the present invention;

FIG. 7 is a graph illustrating sensor output signals of various gas constituents according to the present invention;

FIG. 8 is a graph illustrating constituents of gas in an oral cavity and exhaled breath of a patient having pathological oral malodor, which are analyzed according to the present invention;

FIG. 9 is a graph illustrating constituents of gas in an oral cavity and exhaled breath of a patient having physiological oral malodor, which are analyzed according to the present invention;

FIG. 10 is a graph illustrating a carbon monoxide concentration of gas in an oral cavity and exhaled breath of a smoker, which are measured according to the present invention;

FIG. 11 is a view illustrating an apparatus for analyzing constituents of gas in an oral cavity and exhaled breath according to a second embodiment of the present invention;

FIG. 12 is a view illustrating an apparatus for analyzing constituents of gas in an oral cavity and exhaled breath according to a modified embodiment of the second embodiment of the present invention;

FIG. 13 is a graph comparatively showing an output of a sensor according to the second embodiment of the present invention and an output of a sensor of according to first embodiment of the present invention.

BEST MODE FOR CARRYING OUT THE INVENTION

Figure 1:
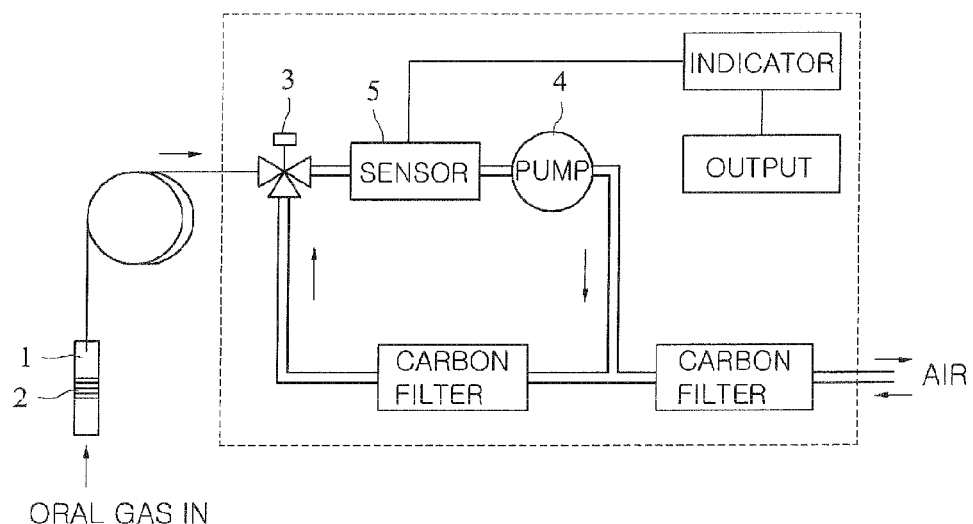
FIG. 1 is a systematic view schematically illustrating a known apparatus for monitoring oral malodor gas.
Figure 2:
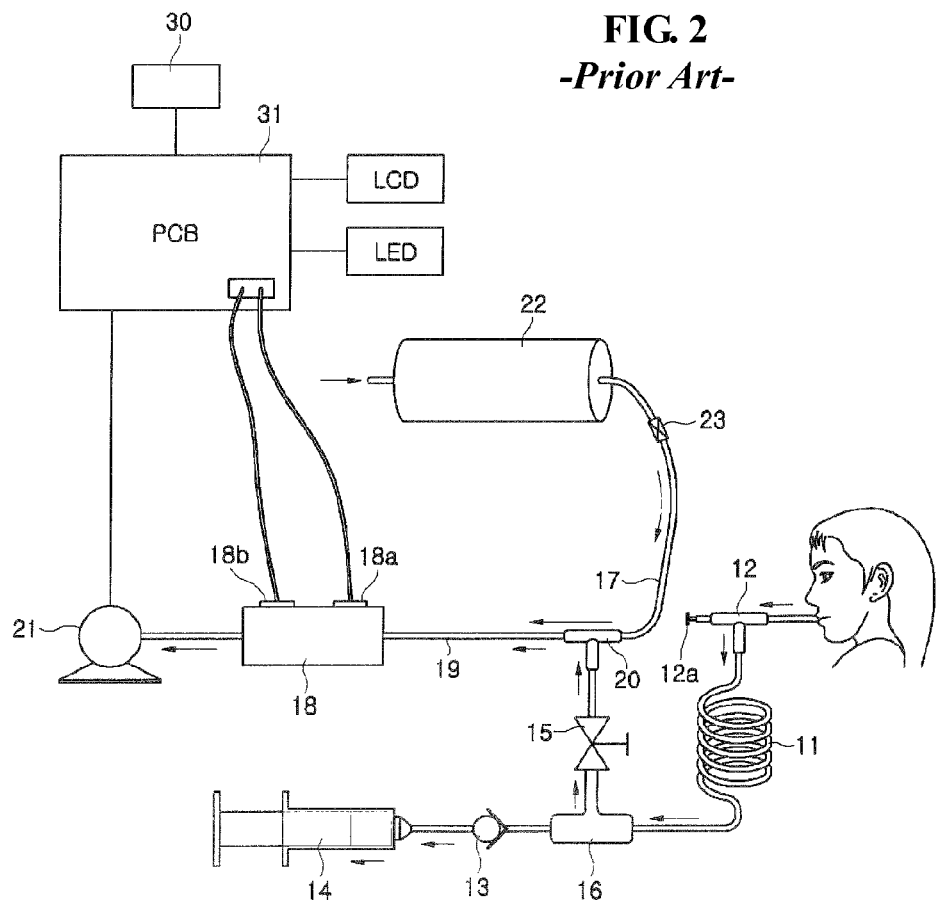
FIG. 2 is a systematic view illustrating another known apparatus for analyzing constituents of oral malodor gas.

Hereinafter, embodiments of the present invention will be described in detail with reference to the accompanying drawings.

FIG. 3 is a view illustrating an apparatus for analyzing constituents of gas in an oral cavity and exhaled breath according to a first embodiment of the present invention, FIG. 4 is a view illustrating an operation of a solenoid valve when gas in an oral cavity is sampled according to the present invention, FIG. 5 is a view illustrating an operation of a solenoid valve during a measuring step after gas in the oral cavity and exhaled breath are sampled according to the present invention, FIG. 6 is a view illustrating an apparatus for analyzing constituents of gas in the oral cavity and exhaled breath according to a modified embodiment of the first embodiment the present invention, and FIG. 7 is a graph illustrating sensor output signals of various gas constituents according to the present invention.

As shown in FIGS. 3 to 7, the apparatus for analyzing the constituents of gas in the oral cavity and exhaled breath according to the present invention includes a filter 110 that is filled with an adsorption and dehumidifying substance such as silica gel, calcium chloride, and activated carbon to filter the outside gas by adsorbing polar molecules and non-polar molecules in the outside air and by removing water in the outside air in order to use the outside gas as carrier gas; a first solenoid valve 120 that is connected to the filter 110 at an end thereof so as to provide carrier gas passing through the filter thereinto and controls a flow of the gas in the oral cavity or the exhaled breath flowing through a connection port 121 thereto; a second solenoid valve 130 that is connected through a connection tube 122 to the first solenoid valve 120 at a first port thereof, connected through a bypass tube 131 to a third solenoid valve 140 at a second port thereof so as to bypass the carrier gas, and connected to a sampling loop 132 filled with the gas in the oral cavity or the exhaled breath collected by the third solenoid valve 140 at a third port thereof; a fourth solenoid valve 150 that is connected through the connection tube 122 to the third solenoid valve 140; a fifth solenoid valve 160 that is connected through an upper bypass tube 161 provided with a speed controller to a port of the fourth solenoid valve 150; a column 162 that is connected to another port of the fourth solenoid valve 150 to allow the gas in the oral cavity or the exhaled breath and the carrier gas to sequentially flow therethrough; a sensor chamber 163 that is connected to the column 162 at an end thereof and has a sensor; a lower bypass tube 164 that is connected to another end of the sensor chamber 163 at an end thereof and to the fifth solenoid valve 160 at another end thereof and is provided with another speed controller; a pump 170 that is connected to the fifth solenoid valve 160 to draw the gas in the oral cavity or the exhaled breath and the carrier gas and then discharge the gas in the oral cavity or the exhaled breath and the carrier gas to the outside; a control unit 180 that is connected to the first to the fifth solenoid valves 120, 130, 140, 150, and 160, the sensor chamber 163, and the pump 170 to control the first to the fifth solenoid valves, the sensor chamber, and the pump; and a display device 190 that measures concentrations of the gases by using signal and calculation treatments in the control unit 180 to display results.

The control unit 180 includes a hardware control unit 181 that is connected to the first to the fifth solenoid valves 120, 130, 140, 150, and 160 and the pump 170 to control the operations of the first to the fifth solenoid valves and the pump, a sensor control unit 182 that is connected to the sensor of the sensor chamber 160 to supply power required to detect sensor signal, and a signal calculation unit 183 that is connected to the sensor of the sensor chamber 160 to determine the type and concentration of the gases after the sensor signal is obtained.

Additionally, in the method of analyzing the constituents of the gas in the oral cavity and the exhaled breath according to the present invention, gas in the oral cavity or exhaled breath is sampled from oral cavities or nasal cavities of humans or domestic animals, and stored in the sampling loop 132. The fresh carrier gas is generated from the filter 110, absorbed by using the pump 170, and inhaled into the column 162 that is filled with the packing material for gas chromatography columns in conjunction with the gas collected in the sampling loop 132 by using the pump 170. As a result, the gas constituents are separated from each other due to a difference in retention time, and the concentrations of the separated gas constituents are measured by the gas sensor.

The apparatus for analyzing the constituents of the gas in the oral cavity and the exhaled breath according to a modified embodiment of the first embodiment, as shown in FIG. 6, further includes a heater 162a to maintain the temperature of the column 162, and a heater control unit 184 that is connected to the heater 162a to control the heater 162a and provided in the control unit 180. The heater control unit maintains the temperature of the heater constantly and adjusts a heating speed of the column at a predetermined rate, thus reducing the retention time of the constituent having the relatively long retention time.

The filter 110 is filled with an adsorption and dehumidifying substance such as silica gel, calcium chloride, and activated carbon in order to filter the air from the outside of the apparatus so that polar and non-polar molecules can be adsorbed and water can be removed from the air.

The carrier gas is fresh dry air which passes through the filter 110, carried to the column 162 along with the sampled gas, and functions to carry the constituents to the sensor when the effective constituent gases transferred on the column 162 are delivered according to the retention time.

The filter 110 and the carrier gas are different from carrier gas which is used in a known gas chromatography, and the differences are as follows. First, in the known gas chromatography, inert gas such as helium, nitrogen, and argon is discharged from a high-pressure cylinder at a high pressure to be used as the carrier gas. For this reason, it is necessary to ensure professionals and specialized rooms in order to operate the high-pressure and high-purity gas cylinder. However, in the present invention, the carrier gas is generated from the air by using the filter 110. For this reason, the generation of carrier gas is easily ensured at low cost as compared to the known gas chromatography. Second, in the known gas chromatography, the carrier gas flows in a flow direction of the high-pressure gas toward the column 162. However, in the present invention, the pump 170 inhales the carrier gas from the filter 110. Like the case of gas chromatography, if the gas which is pressurized by using the pump 170 passes through the filter, the operation time of the apparatus is delayed until the pressure of the gas in the filter 110 reaches the predetermined pressure, and it is necessary to continuously operate the pump 110 in order to maintain the pressure. However, in the present invention, the pump 170 is disposed at the backmost part of the flow of the carrier gas, accordingly, the above-mentioned problems can be avoided. That is, the column 162 that is filled with the packing material requires high pressure in order to enable the carrier gas to flow through the column. As a result, if the pump 110 discharges the carrier gas toward the column 162, the carrier gas is present at a very high positive pressure between the pump 110 and the column 162. On the other hand, like the present invention, if the pump 110 inhales the carrier gas at the rear of the column 162, high negative pressure is applied to the only tube between the column 162 and the pump 110, and the low negative pressure of carrier gas is present at proper level in the filter 170, the solenoid valves 120, 130, 140, 150, and 160, the sampling loop 132 and the like. Accordingly, the carrier gas can be transferred without delaying time inside of the filter. Third, in the known gas chromatography, inert gas such as helium, nitrogen, and argon is used, but in the present invention, the filtered air containing oxygen is used as the carrier gas. Accordingly, the known gas chromatography is different from that of the present invention. The filtered carrier gas supplies oxygen which is required to be used in order to operate the sensor of the present invention.

The sampling loop 132 is made of a material such as PTFE like Teflon which is difficult to adsorb gas thereonto, and has a length that is longer enough than a diameter. The sampling loop is designed so that the old gas existed in the sampling loop is pushed by the new sampled gas when the new gas is additionally sampled and the new sampled gas is inhaled into the sensor between the column 162 and the sensor chamber 163 in order to measure the concentrations of the gas constituents. In the sampling loop 132, the gas is sampled in a precise volume to perform the accurate measurement. sampling over a predetermined period of time which is calculated in consideration of an absorption rate of the pump 170, the gas is transported to the sampling loop 132 having a predetermined volume, the volume of gas is controlled so that the gas is confined in the sampling loop at a desired amount, by the solenoid valve which is closed at a predetermined time. In order to precisely analyze the constituents of the gas, it is necessary to precisely provide the gas at the desired volume to a measurement device. In a known technology using a syringe, it is difficult to precisely control the position of the syringe plunger. Thus, it is difficult to provide the gas in the precise volume. However, in the present invention, if the sampling time is a predetermined value or more, the desired amount of gas is injected to the sampling loop 132 and the excessive amount of gas is discharged through the bypass by using the solenoid valve and the pump. Accordingly, the gas can be sampled in a constant volume conveniently.

Meanwhile, the sampling loop type used in the present invention is different from a known gas chromatography rubber-septum process. In the rubber-septum process, the gas is injected in a relatively small volume of 0.5 to 1.0 ml, and the rubber-septum process is frequently used to perform gas chromatography for special analysis. However, the oral cavity has the volume of several tens of ml. Therefore, it is preferable that the volume of the sampled gas be in the range of 5 to 20 ml, not 0.5 to 1 ml, when the gas in the oral cavity is analyzed. Additionally, in the case of when the gas in the oral cavity is detected like the present invention, the gas constituents which are present in a very small amount of 1 ppm or less are analyzed, and the great volume of analyzed gas constituents contributes to the reliable and precise measurement.

In general, the base line which is an initial value of the sensor varies according to the environment and the measurement conditions during the measurement. In this connection, in the case of when the sampling loop is used like the present invention, the gas constituents are ensured in an amount that is ten times as large as the amount of gas constituents of the rubber-septum case. As a result, a ratio of signal to noise is high and high output signal can be obtained.

The column 162 is filled with the packing materials and has the number of separation stages which are useful to separate the volatile sulfur compounds or the volatile organic compounds and other object gas constituents. The packing material separates the object constituents of the sampled gas by using the retention time caused by a difference in affinity between the packing material and the carrier gas. Particularly, in the known gas chromatography, the gas constituents are carried by the high-pressure carrier gas in the column. However, in the present invention, the gas constituents are carried by using the carrier gas inhaled by using a small vacuum pump in the column. The inner diameter and the length of the column, and the particle size and the packing density of the packing material in the column are different from those of the column of the known gas chromatography.

The sensor of the sensor chamber 163 is used instead of detectors that are required in the known gas chromatography, and is a semiconductor type high-sensitive gas sensor that is formed of a sensor heater and a gas detection film. The sensor has desirable sensitivity and an excellent rapid reaction and recover rate in respects to the retention time. The polymer sensor has poor durability and a short life span and an electrochemical sensor has relatively low sensitivity as compared to the semiconductor type sensor.

Hereinafter, analysis of the constituents of gas in the oral cavity and exhaled breath, and the operation and effect of the apparatus for analyzing the constituents of gas in the oral cavity and exhaled breath according to the present invention will be described. As shown in FIGS. 3 and 4, flows of gas constituents are designated by the full line at a step of sampling the gas in the oral cavity and the exhaled breath, concentrations of which are to be measured. During the sampling step, the first solenoid valve 120 is controlled in the hardware control unit 181 to block the upper port such that the air is not provided to the filter 110. The gas in the oral cavity or the exhaled breath is provided through left and right ports of the first solenoid valve 120 to the second solenoid valve 130, and the sampled gas is provided to the sampling loop 132 that is connected to lower ports of the second solenoid valve 130 and the third solenoid valve 140 at both ends thereof. In this connection, the upper ports of the second and the third solenoid valves 130 and 140 are closed to block the gas flow to the bypass tube 131. As described above, the gas flows to the sampling loop 132 or the air flows through the filter 110 by using the pump 170.

FIGS. 3 and 5 illustrate the concentration measurement of the gas by using the dotted line. That is, in the above-mentioned state, the front port 121 of the first solenoid valve 120 is closed, and the carrier gas is provided to the upper port that is connected to the filter 110 and then to the second solenoid valve 130. The carrier gas is used to follow the sampled gas, that is, the gas in the oral cavity and the exhaled breath, in the sampling loop 132 that is connected to the lower ports of the second and the third solenoid valves 130 and 140 at both ends thereof onto the column 162 that is connected to the lower port of the fourth solenoid valve 150. The effective gas constituents are inhaled onto the column 162, and carried to the sensor of the sensor chamber 163 by using the carrier gas according to the delay time.

The signal calculation unit 183 that is connected to the sensor collects sensor signal to evaluate the state of gas, determine the type and the concentration of gas, and display the type and the concentration of gas on the display device 190.

A gas flow at a recover step for measurement of the next step is designated by the dash-dot line.

The graph of FIG. 7 is a graph which illustrates output signal results of the sensor in respects to the gas constituents. In the graph, the gas constituents such as hydrogen sulfide, methyl mercaptan, acetone, and ethanol have different retention times. That is, the gas constituents can be qualitatively analyzed. In addition, the signals are appropriately detected by using the sensor, resulting in the meaningful signal output magnitude to quantitatively analyze the gas constituents. Meanwhile, in the known gas chromatography, a high-sensitive flame photometric detector (FPD) that is provided with a sulfur filter is frequently used to analyze the gas in the oral cavity. In this case, only the sulfur compounds such as hydrogen sulfide and methyl mercaptan are analyzed. However, in the present invention, a very small amount of sulfur compounds in the gas in the oral cavity and the exhaled breath and volatile organic compounds can be analyzed.

Meanwhile, it is well known that the concentration of carbon monoxide of the exhaled breath of humans is typically measured by the concentration of carbon monoxide of internal hemoglobin. This may be used to objectively evaluate a smoking condition and a smoking dosage of a smoker. According to the present invention, it is possible to measure the concentration of carbon monoxide in the body. A simple measurement method using a gas chromatography for analysis or an electrochemical sensor is used in the related art. In the former case, like the analysis of the oral malodor by using the gas chromatography, professionals, costly equipment, and high maintenance cost are required. For this reason, the former case is difficult to be used in typical hospitals and doctor's offices. In the latter case, there is an advantage in that facilitation is ensured, but an electrochemical sensor is used. For this reason, there is a limit in quantitative measurement, and wrong signal may be outputted due to interference in respects to other types of gases. However, in the present invention, during analysis of the oral malodor and exhaled breath, the concentration of carbon monoxide can be precisely measured along with the sulfur compounds and various types of volatile organic compounds.

For example, FIG. 8 illustrates results of the analysis in respects to a patient having oral malodor according to the present invention. During the analysis of the oral malodor, hydrogen sulfide, methyl mercaptan, and a small amount of carbon monoxide were detected. During the analysis of the exhaled breath, a significant peak signal was not detected. Therefore, it can be seen that the patient is a typical patient having oral malodor who has sulfur compounds in his oral cavity. From the measurement results of methyl mercaptan, it can be seen that the patient has pathological oral malodor. From the low concentration of carbon monoxide, it can be seen that the patient is a nonsmoker.

In FIG. 9, carbon monoxide and hydrogen sulfide are detected in the oral malodor gas, and only carbon monoxide is detected in the exhaled breath. Accordingly, from FIG. 9, it can be seen that the patient is a heavy smoker and has physiological oral malodor because only hydrogen sulfide is detected in the oral malodor gas.

In FIG. 10, only carbon monoxide is detected in the oral malodor gas, and only carbon monoxide is detected in the exhaled breath. However, the heights of the peaks are relatively high. Accordingly, from FIG. 10, it can be seen that the patient does not have oral malodor and is a heavy smoker.

For convenience of the description, the quantitative concentrations of the constituents are omitted in the above. However, if the heights of the peaks are measured, the concentrations of the constituents can be precisely and quantitatively analyzed. The results are shown in FIG. 7.

FIG. 11 is a view illustrating an apparatus for analyzing constituents of gas in an oral cavity and exhaled breath according to a second embodiment of the present invention, FIG. 12 is a view illustrating an apparatus for analyzing constituents of gas in an oral cavity and exhaled breath according to a modified embodiment of the second embodiment of the present invention, and FIG. 13 is a graph comparatively showing an output of a sensor according to the second embodiment of the present invention and an output of a sensor according to the first embodiment of the present invention.

As shown in FIG. 11 and FIG. 12, the apparatus for analyzing constituents of gas in an oral cavity and exhaled breath, comprises a filter 110 that is filled with an adsorption and dehumidifying substance such as silica gel, calcium chloride, and activated carbon to filter the outside gas by adsorbing polar molecules and non-polar molecules in the outside air and by removing water in the outside air in order to use the outside gas as carrier gas, a first solenoid valve 120 that is connected to the filter 110 at an end thereof so as to provide carrier gas passing through the filter thereinto and controls a flow of the gas in the oral cavity or the exhaled breath flowing through a connection port 121 thereto, a sampling loop 132 filled with the gas in the oral cavity or the exhaled breath collected in connection with the first solenoid valve 120, a second solenoid valve 150 that is connected to the sampling loop, a third solenoid valve 160 that is connected to another port of the second solenoid valve 150 through the medium of an upper bypass tube 161 provided with a speed controller, a column 162 that is connected to another port of the second solenoid valve 150 to allow the gas in the oral cavity or the exhaled breath and the carrier gas to sequentially flow therethrough, a sensor chamber 163 that is connected to the column 162 at an end thereof and has a sensor, a lower bypass tube 164 that is connected to another end of the sensor chamber 163 at an end thereof and to the third solenoid valve 160 at another end thereof and is provided with another speed controller, a pump 170 that is connected to the third solenoid valve 160 to draw the gas in the oral cavity or the exhaled breath and the carrier gas and then discharge the gas in the oral cavity or the exhaled breath and the carrier gas to the outside, a control unit 180 that is connected to the first to the third solenoid valves 120, 150 and 160, the sensor chamber 163, and the pump 170 to control the first to the third solenoid valves 120, 150 and 160, the sensor chamber 163, and the pump 170, and a display device 190 that measures concentrations of the gases by using signal and operation processed in the control unit 180 to display the results.

The control unit 180 comprises a hardware controller 181 that is connected to the first to the third solenoid valves 120, 150, and 160 and the pump 170 to control the operations of the first to the third solenoid valves and the pump, a sensor control unit 182 that is connected to the sensor of the sensor chamber 160 to supply power required to detect sensor signal, and a signal calculation unit 183 that is connected to the sensor of the sensor chamber 160 to determine the type and concentration of the gases after the sensor signal is obtained.

Additionally, in the method of analyzing the constituents of the gas in the oral cavity and the exhaled breath according to the present invention, gas in the oral cavity or exhaled breath is sampled from oral cavities or nasal cavities of humans or domestic animals, and stored in the sampling loop 132. The fresh carrier gas is generated from the filter 110, absorbed by using the pump 170, and inhaled into the column 162 that is filled with the packing material for gas chromatography columns in conjunction with the gas collected in the sampling loop 132 by using the pump 170. As a result, the gas constituents are separated from each other due to a difference in retention time, and the concentrations of the separated gas constituents are measured by the gas sensor.

According to the second embodiment of the present invention, the bypass tube 131 adopted in the first embodiment is excluded. In addition, the second and the third solenoid valves in the first embodiment are also omitted.

The second embodiment and the first embodiment of the present invention are applied to respectively different cases, thereby achieving different effects. More specifically, the first embodiment is more appropriate in a case where the carrier gas flown from the outside through the filter contains gas constituents not properly purified and contaminates the sampling loop, since it can minimize contamination of the sampling loop by the carrier gas by transferring the carrier gas to the bypass tube.

On the other hand, the second embodiment is advantageous in terms of removing residues that may remain in the sampling loop by the carrier gas. More particularly, residues may be condensed or attached to an inner surface of the sampling loop in accordance with types and constituents of the collected gas. In this case, the carrier gas is passed through the sampling loop continuously, without being passed through the bypass tube, so that volatile residues in the sampling loop are thoroughly removed. The second embodiment of the present invention has been devised for this purpose, to be improved in the function of the filter such that the carrier gas can be purified thoroughly by the filter.

Thus, the embodiments of the present invention are not superior or inferior to each other, but are just complementary. Therefore, as properly selected according to the cases, the first and the second embodiments are able to draw different effects. Generally, the first embodiment is more appropriate in a case where the collected gas contains a little water, the gas constituents are unlikely to attach to the inside of the sampling loop, and most of the gas constituents are volatile.

However, if the collected gas contains much water or the gas constituents mostly have low volatility, a fresh carrier gas having lower humidity is required in order to volatilize the all residues and remove the water. Furthermore, the sampling loop needs to be exposed to the fresh carrier gas for a longer time. Accordingly, the second embodiment is preferred in this case.

FIG. 13 comparatively shows the cases where the two embodiments are respectively applied, in measuring the oral malodor. According to the graph of FIG. 13, signals of hydrogen sulfide ($H_2S$) and methyl mercaptan ($CH_3SH$) are sequentially output. According to the signal outputs, the second embodiment is superior to the first embodiment since two peaks of the graph are more clearly separated and the state of the peaks are more excellent.

The invention claimed is:

1. An apparatus for analyzing constituents of a gas in an oral cavity and an exhaled breath, the apparatus comprising:
a filter, filled with a substance adsorbing a polar molecule and a non-polar molecule comprising silica gel and activated carbon, to filter an air;
a first solenoid valve connected to the filter so as to provide the air passing through the filter thereinto and to control a flow of the gas in the oral cavity or the exhaled breath flowing through a connection port thereto;
a second solenoid valve connected through a first connection tube to the first solenoid valve at a first port thereof, connected through a bypass tube to a third solenoid valve at a second port thereof so as to bypass the air, and connected through a sampling loop to the third solenoid valve at a third port thereof, the sampling loop filled with the gas in the oral cavity or the exhaled breath which is collected;
a fourth solenoid valve connected through a second connection tube to the third solenoid valve;
a fifth solenoid valve connected through an upper bypass tube provided with a speed controller to a port of the fourth solenoid valve;
a column that is filled with a packing material for gas chromatography columns and that is connected to another port of the fourth solenoid valve to allow the gas in the oral cavity or the exhaled breath and the air to sequentially flow therethrough;
a sensor chamber comprising a sensor connected to the column at an end thereof;
a lower bypass tube connected to another end of the sensor chamber at an end thereof and to the fifth solenoid valve at another end thereof, the lower bypass tube provided with another speed controller;
a suction pump configured at the rear portion of the column and connected to the fifth solenoid valve to draw the gas in the oral cavity or the exhaled breath and the air and then discharge the gas in the oral cavity or the exhaled breath and the air to the outside;
a control unit connected to the respective solenoid valves, the sensor chamber, and the suction pump to control the respective solenoid valves, the sensor chamber, and the suction pump; and
a display device to output results of concentrations of the gases measured by using signal and calculation treatments,
wherein the control unit performs a sampling step, a measurement step, and a recovering step according to the following steps:
when in the sampling step, the control unit operates:
to close a first portion to the filter and to open a second portion to the connection port of the first solenoid valve,
to close the second port which is connected to a bypass tube of the second solenoid valve, to open the third port which is connected to a sampling loop of the second solenoid valve, to open the third solenoid valve, to open a first port which is connected to an upper bypass tube of the fourth solenoid valve, and to close a second port which is connected to the column of the fourth solenoid valve;

when in the measurement step, the control unit operates:

to open the fifth solenoid valve, wherein the suction pump is activated, and the gas in an oral cavity is caused to be inhaled into the sampling loop, the control unit further operates to open the first portion to the filter and to close the second portion to the connection port of the first solenoid valve, to close the second port which is connected to the bypass tube of the second solenoid valve and to open the third port which is connected to the sampling loop of the second solenoid valve, to open the third solenoid valve, to close a first port which is connected to the upper bypass tube of the fourth solenoid valve, and to open a second port which is connected to the column of the fourth solenoid valve, to open the fifth solenoid valve, wherein the suction pump is activated and the air is caused to be inhaled into the sampling loop and thereby the oral cavity and the exhaled breath is to be inhaled and passed through the column; and when in the recovering step, the control unit operates:

to open the first portion to the filter and to close the second portion to the connection port of the first solenoid valve, to open the second port which is connected to a bypass tube of the second solenoid valve and to close the third port which is connected to the sampling loop of second solenoid valve, to open the third solenoid valve, to close a first port which is connected to the upper bypass tube of the fourth solenoid valve and to open a second port which is connected to the column of the fourth solenoid valve, and to open the fifth solenoid valve, wherein the suction pump is activated, and the air is caused to be inhaled and passed through the column.

2. The apparatus according to claim 1, wherein the control unit includes:

a hardware control unit connected to the respective solenoid valves and the suction pump to control operations of the respective solenoid valves and the suction pump;

a sensor control unit connected to the sensor of the sensor chamber to supply power required to detect sensor signal; and a signal calculation unit connected to the sensor of the sensor chamber to determine a type and a concentration of the gases after the sensor signal is obtained.

3. The apparatus according to claim 1, further comprising:
a heater to maintain and control a temperature of the column.

4. The apparatus according to claim 3, further comprising:
a heater control unit connected to the heater in the control unit to control the heater so that a temperature of the heater is increased and decreased at a predetermined rate.

5. The apparatus according to claim 3, further comprising:
a heater control unit connected to the heater in the control unit to control the heater so that a temperature of the heater is increased and decreased at a predetermined rate.

6. The apparatus according to claim 2, wherein measurement data of the gas collected from the oral cavity and measurement data of the exhaled breath collected from a nose are compared to each other in the signal calculation unit, and a difference in measurement data is compared to a pre-inputted pattern to determine whether a cause of oral malodor is an oral cavity disease or an internal disease.

7. A method of analyzing constituents of a gas in an oral cavity and an exhaled breath, the method comprising:

in response to detection of a sampling step by a control unit, closing a filter side and opening a connection port of a first solenoid valve, closing a second port which is connected to a bypass tube of a second solenoid valve and opening a third port which is connected to a sampling loop of the second solenoid valve;

opening a third solenoid valve, opening a first port which is connected to an upper bypass tube of a fourth solenoid valve and closing a second port which is connected to the column of the fourth solenoid valve;

in response to detection of a measurement step by the control unit, opening a fifth solenoid valve, wherein a suction pump is activated, and the gas in an oral cavity and exhaled breath is caused to be inhaled and passed the sampling loop, opening the filter side and closing the connection port of first solenoid valve, closing the second port which is connected to the bypass tube of the second solenoid valve and opening the third port which is connected to the sampling loop of the second solenoid valve, opening the third solenoid valve, closing a first port which is connected to the upper bypass tube of the fourth solenoid valve and opening a second port which is connected to the column of the fourth solenoid valve, opening the fifth solenoid valve, wherein the suction pump is activated, and the air is caused to be inhaled into the sampling loop and thereby the oral cavity and an exhaled breath is to be inhaled and passed the column; and in response to detection of a recovering step by the control unit, opening the filter side and closing the connection port of first solenoid valve, opening the second port which is connected to the bypass tube of second solenoid valve and closing the third port which is connected to the sampling loop of the second solenoid valve, opening the third solenoid valve, closing a first port which is connected to the upper bypass tube of the fourth solenoid valve and opening a second port which is connected to the column of the fourth solenoid valve, and opening the fifth solenoid valve, wherein the suction pump is activated, and the air is caused to be inhaled and passed through the column.

8. The method according to claim 7, further comprises:
comparing measurement data of oral malodor gas collected from the oral cavity and measurement data of the exhaled breath collected from a nose to each other to determine whether a cause of oral malodor is an oral cavity disease or an internal disease.

9. The method according to claim 7, further comprises:
measuring a concentration of carbon monoxide contained in the exhaled breath and the gas in the oral cavity by using a gas sensor.

10. An apparatus for analyzing constituents of a gas in an oral cavity and an exhaled breath, the apparatus comprising:

a filter, filled with a substance comprising silica gel and activated carbon, to filter off an air of the outside;

a first solenoid valve connected to the filter at an end thereof so as to provide the air passed through the filter thereinto and to control a flow of the gas in the oral cavity or the exhaled breath flowing through a connection port thereto;

a sampling loop connected with the first solenoid valve;

a second solenoid valve connected to the sampling loop;
a third solenoid valve connected to a port of the second solenoid valve through the medium of an upper bypass tube provided with a speed controller;
a column connected to another port of the second solenoid valve to allow the gas in the oral cavity or the exhaled breath and the carrier gas to sequentially flow therethrough;
a sensor chamber connected to the column at an end thereof and has a sensor; a lower bypass tube connected to another end of the sensor chamber at an end thereof and to the third solenoid valve at another end thereof and is provided with another speed controller;
a suction pump configured at the rear portion of the column and connected to the third solenoid valve to draw the gas in the oral cavity or the exhaled breath and the air and then discharge the gas in the oral cavity or the exhaled breath and the air to the outside, a control unit connected to the respective solenoid valves, the sensor chamber, and the pump to control the respective solenoid valves, the sensor chamber, and the pump; and
a display device to output results of concentrations of the gases measured by using signal and operation processed in the control unit,
wherein the control unit is configured to perform a sampling step, a measurement step, and a recovering step according to the following steps:
when in the sampling step, the control unit operates:
to close a first portion to the filter and to open a second portion to the connection port of the first solenoid valve, to close the second port which is connected to a bypass tube of the second solenoid valve, to open the third port which is connected to a sampling loop of the second solenoid valve, to open the third solenoid valve, to open a first port which is connected to an upper bypass tube of the fourth solenoid valve, and to close a second port which is connected to the column of the fourth solenoid valve;
when in the measurement step, the control unit operates:
to open the fifth solenoid valve, wherein the suction pump is activated, and the gas in an oral cavity is caused to be inhaled into the sampling loop, the control unit further operates to open the first portion to the filter and to close the second portion to the connection port of the first solenoid valve, to close the second port which is connected to the bypass tube of the second solenoid valve and to open the third port which is connected to the sampling loop of the second solenoid valve, to open the third solenoid valve, to close a first port which is connected to the upper bypass tube of the fourth solenoid valve, and to open a second port which is connected to the column of the fourth solenoid valve, to open the fifth solenoid valve, wherein
the suction pump is activated and the air is caused to be inhaled into the sampling loop and thereby the oral cavity and the exhaled breath is to be inhaled and passed through the column; and
when in the recovering step, the control unit operates:
to open the first portion to the filter and to close the second portion to the connection port of the first solenoid valve, to open the second port which is connected to a bypass tube of the second solenoid valve and to close the third port which is connected to the sampling loop of second solenoid valve, to open the third solenoid valve, to close a first port which is connected to the upper bypass tube of the fourth solenoid valve and to open a second port which is connected to the column of the fourth solenoid valve, and to open the fifth solenoid valve, wherein
the suction pump is activated, and the air is caused to be inhaled and passed through the column.

11. The apparatus according to claim 10, further comprises:
a hardware control unit connected to the respective solenoid valves and the pump to control operations of the respective solenoid valves and the pump;
a sensor control unit connected to the sensor of the sensor chamber to supply power required to detect sensor signal; and
a signal calculation unit connected to the sensor of the sensor chamber to determine a type and a concentration of the gases after the sensor signal is obtained.

12. The apparatus according to claim 11, further comprising:
a heater is configured to maintain and to control a temperature of the column.

13. The apparatus according to claim 12, further comprising:
a heater control unit connected to the heater in the control unit to control the heater so that a temperature of the heater is increased and decreased at a predetermined rate.

14. The apparatus according to claim 10, wherein measurement data of the gas collected from the oral cavity and measurement data of the exhaled breath collected from a nose are compared to each other in the signal calculation unit, and a difference in measurement data is compared to a pre-inputted pattern to determine whether a cause of oral malodor is an oral cavity disease or an internal disease.

* * * * *